United States Patent [19]

Sandhu et al.

[11] Patent Number: 5,580,494

[45] Date of Patent: Dec. 3, 1996

[54] HAIR CONDITIONING SHAMPOO CONTAINING HIGH CHARGE DENSITY POLYMERS

[75] Inventors: Sukhvinder S. Sandhu, Plainsboro; Clarence R. Robbins, Martinsville; Wei-Ming Cheng, Piscataway; Amrit Patel, Dayton, all of N.J.

[73] Assignee: Colgate-Palmolive Company, Piscataway, N.J.

[21] Appl. No.: 186,245

[22] Filed: Jan. 25, 1994

Related U.S. Application Data

[63] Continuation-in-part of Ser. No. 948,518, Sep. 22, 1992, abandoned, which is a continuation-in-part of Ser. No. 507,335, Apr. 9, 1990, Pat. No. 5,213,716, which is a continuation-in-part of Ser. No. 369,361, Jun. 21, 1989, abandoned, Ser. No. 369,389, Jun. 21, 1989, abandoned, Ser. No. 432,644, Nov. 7, 1989, Pat. No. 5,051,250, and Ser. No. 432,952, Nov. 7, 1989, abandoned.

[51] Int. Cl.$^6$ ....................................................... C11D 1/83
[52] U.S. Cl. ........................... 510/125; 510/126; 510/127
[58] Field of Search ...................................... 252/117, 121, 252/555, 173, 174.15, 174.23, 547, 542, 174.21, 550; 424/70

[56] References Cited

U.S. PATENT DOCUMENTS

| | | | |
|---|---|---|---|
| 4,832,872 | 5/1989 | Scandel | 252/547 |
| 4,871,536 | 10/1989 | Arraudeau et al. | |
| 5,037,632 | 8/1991 | Gross et al. | 424/47 |
| 5,152,914 | 10/1992 | Forster et al. | 252/174 |

FOREIGN PATENT DOCUMENTS

| | | | |
|---|---|---|---|
| 0437114 | 12/1990 | European Pat. Off. | A61K 7/075 |
| 0413417 | 2/1991 | European Pat. Off. | |
| 0463780 | 1/1992 | European Pat. Off. | A61K 7/06 |
| 0511652 | 11/1992 | European Pat. Off. | A61K 7/06 |
| 0522755 | 1/1993 | European Pat. Off. | A61K 7/06 |
| 0531650 | 3/1993 | European Pat. Off. | A61K 7/06 |
| 2585947 | 2/1987 | France | A61K 7/09 |
| 56-72095 | 6/1981 | Japan . | |
| 2193971 | 8/1987 | United Kingdom | C11D 1/29 |
| 9210162 | 6/1992 | WIPO . | |
| 9308787 | 10/1992 | WIPO | A61K 7/06 |
| 9401077 | 6/1993 | WIPO | A61K 7/06 |

OTHER PUBLICATIONS

Kosmetika Aerosole Riechstoffe; Journal: Seifen, Oele, Fette, Wachse; 1984, vol. 110, No. 17, pp. 515–516; "Luviquat brands (CTFA: Polyquaternium 16). New polyquaternary polymers with different degrees of cationic activity"; Seib, Vogel. *No month available.

Les Luviquat: cationiques pour soins capillaires; Journal: Parfums, Cosmet., Aromes; 1988, vol. 83, pp. 99–100, 102; "Cationic Luviquats for hair care"; Frosch *No month available.

Patent Abstracts of Japan vol. 13, No. 461 (C–645) (3809) Oct. 18, 1989–JP 1–180813 Shiseido Co. Ltd.

*Primary Examiner*—Paul Lieberman
*Assistant Examiner*—Necholus Ogden
*Attorney, Agent, or Firm*—James M. Serafino; Richard J. Ancel

[57] ABSTRACT

An aqueous hair conditioning shampoo comprising a hair-cleansing effective amount of an anionic surfactant comprising an alpha-olefin sulfonate, a hair-conditioning effective amount of a cationic polymer having a hair conditioning effect and a charge density greater than about 200, a water-insoluble hair conditioning agent and a dispersing agent which functions to stabilize the emulsion or suspension, and the remainder water.

13 Claims, No Drawings

HAIR CONDITIONING SHAMPOO CONTAINING HIGH CHARGE DENSITY POLYMERS

RELATED APPLICATIONS

This application is a continuation-in-part of application U.S. Ser. No. 07/948,518, filed Sep. 22, 1992, abandoned, which is a continuation-in-part of U.S. Ser. No. 07/507,335, filed Apr. 9, 1990, now U.S. Pat. No. 5,213,716, which is a continuation-in-part of U.S. Ser. No. 07/369,361, filed Jun. 21, 1989, abandoned, U.S. Ser. No. 07/369,389, filed Jun. 21, 1989, abandoned, U.S. Ser. No. 07/432,644, filed Nov. 7, 1989, now U.S. Pat. No. 5,051,250, and U.S. Ser. No. 07/432,952, filed Nov. 7, 1989, abandoned.

BACKGROUND OF THE INVENTION

1. Field of the Invention

The present invention relates to shampoos containing polymeric hair conditioning agents.

2. The Prior Art

Conventional hair conditioning shampoos generally comprise one or more anionic surfactants such as sodium or ammonium lauryl sulfate or laureth sulfate to wash off oil and dirt from the hair and one or more hair conditioning agents to enhance combability and lustre, detangle the hair, reduce static electricity, etc. Among the hair conditioning agents traditionally incorporated in hair conditioning shampoos are water-insoluble silicones (e.g., dimethicone) and cationic polymers with quaternary moieties.

The latter readily adhere to hair because of the inherent anionic change in individual hair fibers. However, the cationic nature of the polymers also contribute to instability of the shampoo formulation because of the anionic nature of the surfactant. The mutual attraction between the anionic surfactant and the cationic polymer results in reduced deposition of the polymer in the hair, cloudiness in the shampoo product and a reduction in the foamability of the shampoo.

It would be desirable to increase the charge density of the cationic polymers to further enhance the attraction thereof and adherence to the anionic keratin hair fibers. However, increasing the charge density also exacerbates the disadvantages noted above connected with the use of cationic polymers in formulations containing anionic agents.

It has been common practice to employ water-insoluble silicones in conjunction with cationic polymers as co-hair conditioners to alleviate some of the disadvantages associated with the latter since they carry no charge and do not interact with anionic surfactants. The addition of silicones, however, adds to the complexity of the final mixture, rendering it less stable as well as increasing the cost of the final shampoo product.

Moreover, the anionic surfactants conventionally employed in hair conditioning shampoos, i.e., the salts of lauryl sulfate and laureth sulfate, are somewhat harsh to hair fibers in that they tend to dissolve some of the hair protein.

It is an object of the present invention to provide a stable hair conditioning shampoo comprising an anionic surfactant and a high charge density cationic polymer hair conditioner which enables the elimination of or at least a reduction in the amount of water-insoluble silicone hair conditioning agent, which is highly adherent to hair fibers and which is less harsh to hair protein than conventional hair conditioning shampoos.

SUMMARY OF THE INVENTION

These and other objects are realized by the present invention, one embodiment of which relates to an aqueous hair conditioning shampoo comprising:

(i) a hair-cleansing effective amount of an anionic surfactant comprising an alpha-olefin sulfonate;

(ii) a hair-conditioning effective amount of a cationic polymer having a hair-conditioning effect and a charge density greater than about 200;

(iii) a hair-conditioning effective amount of a dispersed water-insoluble hair-conditioning agent;

(iv) an amount of at least one dispersing agent sufficient to stabilize the aqueous shampoo in emulsion or suspension form; and (v) the remainder water.

DETAILED DESCRIPTION OF THE INVENTION

The present invention is predicated on the discovery that hair conditioning shampoo compositions containing alpha-olefin sulfonate anionic surfactants can tolerate significant amounts of high charge density cationic polymer hair conditioning agents without detriment to the stability of the system. The ability to employ larger amounts of the high charge density cationic polymer also enables the utilization of less or no water-insoluble co-hair conditioning agents such as silicones, etc.

A further advantage associated with the hair conditioning shampoos of the invention is that the alpha-olefin sulfonate surfactants employed therein are less harsh to the hair fibers, i.e., they dissolve much less hair protein than conventionally employed anionic surfactants.

Any cationic polymer having hair conditioning properties may be employed in the practice of the invention provided that it has a charge density greater than about 200, more preferably, greater than about 180 (the lower the number, the higher the charge density).

The charge density of a cationic polymer is given by the formula:

$$\frac{\text{formula cation molecular weight}}{\text{\# of positive charges}}$$

Suitable such cationic polymers include copolymers of vinylimidazole (VI) and vinylpyrrolidone (VP) wherein the molar ratio of VI to VP is at least about 1:1, most preferably from about 5:1 to about 20:1. A particularly suitable such polymer is LUVIQUAT FC 905 (CTFA designation: Polyquaternium 16) which is a copolymer of 95% VI and 5% VP.

Another class of suitable cationic polymers are the homopolymers of dialkyldiallylammonium halides wherein the alkyl group may contain from 1 to 5 carbon atoms. A particularly preferred polymer in this class is the homopolymer of dimethyldiallylammonium chloride, commercially available under the tradename MERQUAT 100 (CTFA designation: Polyquaternium 6).

Polyethyleneimine is another suitable high charge density cationic polymer.

It will be understood that mixtures of suitable cationic polymers may also be employed.

As noted above, in order to employ sufficiently large amounts of these high charge density cationic polymers in shampoos to impart hair conditioning properties to the formulation, it is necessary to incorporate therein as anionic surfactants, alpha-olefin sulfonates. The alpha-olefin sulfonates are a well-known class of surfactants. More specifically, they comprise a mixture of hydroxyalkane sulfonates and alkene sulfonates derived from $C_{14}$–$C_{18}$ alpha-olefins.

Many surfactants are harsh to hair and skin in that they tend to dissolve protein therefrom. So-called "milder" surfactants dissolve the least amount of protein from hair and skin.

Studies have shown that the alpha-olefin sulfonates are less harsh and milder to hair than most other commonly employed shampoo surfactants such as ammonium and sodium lauryl sulfate and sodium and ammonium laureth sulfate.

It has been further unexpectedly found that the ammonium salts of the alpha-olefin sulfonates are milder to hair than the alkali metal, particularly the sodium, salts thereof.

In a most preferred embodiment of the invention, therefore, it is preferred to include in the hair conditioning shampoos of the invention suitable dispersing agents for stabilizing the emulsion or suspension containing the surfactants, cationic polymer and other ingredients. Exemplary of such dispersing agents are long chain saturated primary aliphatic alcohols or derivatives thereof having an average of 24 to 45 carbon atoms in the chain; long chain acylated compounds, e.g., esters, acids or amides with at least 18 carbon atoms such as syncrowax HGL-C, beeswax, etc.

Suitable long chain primary aliphatic alcohols which may constitute the dispersing agent in the shampoo of the invention are saturated compounds with the hydroxy group being terminally located. Such alcohols will normally be of a distribution of homologous alcohols and typically all are of even numbers of carbon atoms, averaging 24 to 45 atoms (on a weight basis), preferably 28 to 42 carbon atoms, and more preferably about 30 to 40 carbon atoms. When the average number of carbon atoms in the chain is less than 24, the desired effectiveness of such alcohols in the present formulations is decreased, with the stabilization, fiber conditioning and pearlescing actions being diminished. When such chain length is more than 45 carbon atoms, e.g., of an average of about 50 carbon atoms, such alcohols are not satisfactorily dispersible in the described compositions.

In addition to the aforementioned long chain alcohols, related compounds such as corresponding alkoxylated alcohols, corresponding fatty acids and long chain saturated primary alcohol esters may be substituted, at least in part. Of such "derivatives," the alkoxylated alcohols are preferred, and the most preferred of these are the ethoxylated alcohols which will normally contain up to about 20 ethoxy groups per mole, e.g., about 10 to 20. However, the alcohols which are the preferred embodiments of the invention normally will be employed alone or in mixture with related compounds from the "derivatives" group, with the alcohol being the major proportion of the total "alcohol plus derivatives" content. Examples of commercial materials which may be employed in the present compositions are those manufactured by Petrolite Corporation and sold through their Petrolite Specialty Polymers Group under the name Unilin™ Alcohols as described in the technical bulletin of the Petrolite Corporation entitled "Unilin™ Alcohols" copyrighted in 1985 and identified as SP-1040. Such alcohols may be 75 to 90%, e.g., 80 to 85%, of the commercial product, with the balance of such products being substantially all saturated hydrocarbons of corresponding chain lengths. In such products, the distribution curve for the alcohol is substantially bell-shaped, with no chain length of alcohol being more than 10% of the total content thereof and with the corresponding hydrocarbon content being of a substantially flat distribution curve, with about 1 or 2% of each of the hydrocarbons being present. Such distribution curves, as bar graphs, are provided in the Petrolite bulletin mentioned above. The alcohols (and corresponding hydrocarbons) present will normally be of chain lengths such that at least 80% are in the range of 18 or 20 to 54 carbon atoms, with at least 80% being in the range of about 18 or 20 to 44 carbon atoms for an alcohol averaging about 30 carbon atoms, and with at least 80% being in the range of about 28 or 30 to 54 carbon atoms when the alcohol averages about 40 carbon atoms. Examples of the long chain primary alcohols are Unilin-425 alcohol which averages 30 carbon atoms in its chain, Unilin-550 alcohol which averages 40 carbon atoms in its chain, and Unilin-350 which averages about 26 carbon atoms in its chain. A derivative, Unithox-550, is an ethoxylated such alcohol having an average of 40 carbon atoms in the alkyl chain, ethoxylated with up to 20 ethoxy groups, e.g., 13.

Suitable long chain acyl derivatives useful as dispersing agents in the shampoos of the invention include those described in U.S. Pat. No. 4,741,885, the entire content of which is incorporated herein by reference, e.g., ethylene glycol esters of fatty acids having from about 16 to about 22 carbon atoms. Other acyl derivatives which are useful are alkanolamides of fatty acids having from about 16 to about 22 carbon atoms, and preferably about 16 to 18 carbon atoms, e.g., stearic monoethanolamide, stearic diethanolamide, stearic monoisopropanolamide, stearic monoethanolamide stearate, etc. Also useful are long chain esters of long chain fatty acids such as stearyl stearate, cetyl palmitate, etc.; glyceryl ester, e.g., glyceryl distearate; and long chain esters of long chain alkanolamides, e.g., stearamide DEA distearate, stearamide MEA stearate, etc.

Additionally useful dispersing agents include the alkyl ($C_{16}$–$C_{22}$) dimethyl amine oxides, e.g., stearyl dimethyl amine oxide.

Cross-linked anionic synthetic polymers may also be used as dispersing agents in the practice of the invention, e.g., polyacrylic acid or polymethacrylic acid polymers or copolymers or derivatives thereof with other olefinic comonomers or compounds with a lipophilic side group; and polymers of vinyl sulfonic acid or derivatives or comonomers compatible with the objects of the present invention, e.g., polyvinylsulfate, polystyrene sulfonate, etc.

Additionally useful dispersing agents are polysaccharides or quaternized derivatives thereof such as hydroxyethylcellulose or methyl cellulose, guar gum, xanthan gum or quaternized derivatives of the above such as polymer JR or cationic guar gum; and alkyl dimethyl amine oxides, the alkyl group having from about 8 to about 18 carbon atoms.

Additional suitable dispersing agents are those described in U.S. Pat. No. 4,997,641 and U.S. patent application Ser. No. 07/507,335 filed Apr. 9, 1990, now U.S. Pat. No. 5,213,716.

Preferably, the dispersing agent is selected so as to render the emulsion or suspension pearlescent.

It is also preferred to include a co-hair conditioning amount of a water-insoluble hair conditioning agent to impart optional hair conditioning properties to the shampoo formulations of the invention, although it will be understood that smaller amounts of the water-insoluble hair conditioning agents are required than in conventional hair conditioning shampoo compositions.

Suitable water-insoluble hair conditioning agents for use in the hair conditioning shampoos of the present invention include silicones, aminosilicones, polyalkylenes and oxidized derivatives thereof, mineral oils, paraffins, petrolatums, microcrystalline waxes, $C_{18-36 \ (mixed)}$ fatty acids and mixed triglycerides thereof and stearyl stearate (and other higher esters), as well as mixtures thereof.

The organosilicon compounds and the silicones that may be employed in the practice of the present invention include any of those which are hair conditioning agents intended for use in conditioning shampoos, various of which have been described in the patents mentioned hereinabove. They are preferably of non-volatile types. It has been found that aminosilicones are usually more effective conditioning agents in the compositions of this invention than are conventional silicones and, of the aminosilicones, the present special types described herein are better yet. Thus, it is much preferred to utilize an aminosilicone of the formula:

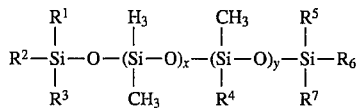

wherein $R^1$, $R^2$, $R^3$, $R^5$, $R^6$ and $R^7$ are alkyls of 1 to 6 carbon atoms, and most preferably of 1 carbon atom each. $R^4$ is —$R^8$—NH—$CH_2CH_2$—$NH_2$, $R^8$ is alkylene of 3 to 6 carbon atoms and most preferably is an isobutyl group, x is an average number in the range of 1 to 10, more preferably less than 5 and most preferably 1, which is of an amine equivalent in the range of 4,000 to 60,000. Preferably, x is in the range of 200 or 300 to 10,000, more preferably 500 to 10,000 and most preferably 750 to 800 or 850, e.g., about 800, and y is in the range of 0 to 8, more preferably being less than 3 and most preferably being about 1. The amine equivalent of such aminosilicone is preferably in the range of 5,000 to 50,000, and more preferably 10,000 to 40,000. For the specific preferred aminosilicone utilized in the experiments reported herein, the molar percentage of amine is about 0.125, the degree of polymerization is about 800, x is 797, y is one and the molecular weight is about 60,000 daltons. Because molecular weights of high polymers sometimes vary, depending on the measurement technique utilized, it is suggested that primary reference should be to the formula for identification of the aminosilicones described, rather than placing primary reliance on the molecular weights provided.

The polyalkylenes that may be employed in the present invention as water-insoluble conditioning agents are preferably those of a molecular weight in the range of 1,000 to 5,000, more preferably 1,000 to 4,000 and most preferably 2,000 to 2,500, e.g., about 2,000. Oxidized versions of these polyalkylene polymers may also be used which create larger hydrocarbons with terminal carboxyl groups. Although the alkylenes of these polymers will usually be ethylene, it is within the scope of the present invention to employ polymers of hydrocarbons of 2 to 5 carbon atoms each, and preferably 2 to 3 carbon atoms, in which the molecular weight range may be from 1,000 to 10,000 or even more under some conditions. Usually, however, the polymers will be of ethylene and/or propylene, and almost always of ethylene.

Paraffins that may be utilized will normally be of chain lengths of 20 to 50 carbon atoms, and preferably 20 to 40 carbon atoms, and isoparaffins can be of chain lengths in the range of 12 to 16 carbon atoms, and preferably 13 to 14 carbon atoms. The petrolatums are petroleum jellies or mineral jellies which melt in the range of 38° C. to 60° C. and the microcrystalline waxes are of an average molecular weight in the range of about 500 to 800 (which is about twice that of the paraffins). $C_{18-36 \ (mixed)}$ fatty acid triglycerides are higher triglycerides which are available from Croda Chemical Corporation under the tradename Syncrowax (HGL-C, for example). Stearyl stearate, which is representative of useful esters of both higher fatty alcohols and higher fatty acids, is available from Inolex Corporation as Lexol SS. This and related compounds such as other high fatty esters may also act as stabilizers for the shampoo composition, preventing settling out of components and phase separations.

Further examples of suitable water-insoluble conditioning agents are set forth in U.S. patent application Ser. No. 07/507,335 filed Apr. 9, 1990, now U.S. Pat. Nos. 5,213,716 and 4,997,641, the entire contents of both being incorporated herein by reference.

The hair conditioning shampoos of the present invention may comprise:

(i) from about 4 to about 40%, and preferably from about 10 to about 25%, of an anionic surfactant comprising an alpha-olefin sulfonate;

(ii) from about 0.3 to about 6%, and preferably from about 0.5 to about 2%, of a cationic polymer having a hair conditioning effect and a charge density greater than 180;

(iii) from about 0.3 to about 8%, and preferably from about 0.5 to about 4%, of a dispersed water-insoluble hair conditioning agent;

(iv) from about 0.3 to about 8%, and preferably from about 1 to about 5%, of at least one dispersing agent which functions to stabilize the emulsion or suspension; and (v) the remainder water.

To make the compositions of the present invention, the various required components are dissolved and/or suspended in an aqueous medium. Such medium may include various non-interfering normal shampoo composition constituents or adjuvants known in the art, but a few of these will be specifically mentioned herein because they are especially desirable components of the present compositions and contribute in a significant manner to its desirable properties. Higher fatty alkanolamides having long been-known as foaming agents and foam stabilizers. Such compounds will usually be of 12 to 16 carbon atoms in the acyl group which is reacted with a lower (1 to 3 carbon atoms) mono- or dialkanolamine. In the present formulations, the best alkanolamides are considered to be lauric monoethanolamide and cocoethanolamide. However, other known foam stabilizers and foaming agents may also be employed in whole or in part such as the betaines and related materials. Various gums and other thickening materials are also useful in shampoo compositions, but it has been found that the best of these in the present compositions are hydroxyethyl celluloses. Such materials are available from Aqualon Corporation under the trademark NATROSOL, such as NATROSOL 250 HHR and NATROSOL 330 CS, which preferably are employed in mixture, with the content of the former being from two to five times that of the latter. However, other suitable gums and thickeners may be also be employed such as hydroxypropylmethyl cellulose, methyl cellulose, modified starches and guar gum. Another important constituent of the present composition is mineral oil when polyethylene is employed as a hair conditioning agent. The mineral oil is employed to solubilize and help disperse the polyethylene which, if not satisfactorily dispersed in the composition, will be of little hair conditioning effect and tends to settle out.

Other components of the present compositions which may be employed include ethylene glycol monostearate, ethylene glycol distearate and propylene glycol distearate, all of which have pearlescing properties; viscosity control agents such as propylene glycol and sodium chloride; pH adjusting agents such as citric acid and citrates; sequestrants such as EDTA; antifreezes such as propylene glycol; solvents such as ethanol and isopropanol; preservatives and anti-oxidants, such as Germaben II (Sutton Laboratories); anti-dandruff agents such as zinc pyrithione and Climbazole™ (see U.S. Pat. No. 4,867,971); colorants and perfume. Water, employed to make the aqueous medium but which may be present not only in liquid preparations but also in gels, pastes and cremes, is preferably filtered, irradiated and deionized water of essentially zero hardness, but it may also be tap water, although it is preferred to keep the hardness below 50 ppm, as calcium carbonate. However, other tap waters of hardnesses as high as 200 ppm will sometimes also be useful, but usually they should be avoided.

All percentages of components expressed herein, unless other indicated, are by weight, based on the weight of the composition in which the component is present.

The invention is illustrated by the following non-limiting examples.

The following procedure was employed to formulate the compositions set forth in the examples hereinbelow.

The required amounts of deionized water, ammonium AOS, ammonium phosphate and citric acid are weighed in a glass beaker and the contents are heated to 90° C. while stirring with a variable speed Lightnin mixer at 300–500 rpm. In a separate beaker, the required amounts of distearyl dimethylammonium chloride long chain alcohols and cocodiethanolamide are weighed and heated to 90° C. while mixing until all the material is melted to a uniform phase. The oil phase is added to the ammonium AOS solution, taking care not to promote foam and mixing is continued for fifteen minutes at 90° C. The batch is then cooled to 72° C. while mixing. The formula weight of silicone is added and the batch is mixed for fifteen minutes. With continuous mixing for at least fifteen minutes, the high charge density cationic polymer is added to the batch and thereafter cooled to 52° C. The formula weight of perfume is then added while mixing is continued and the mixture is cooled to 38° C. The formula amounts of preservative and colors are added and the batch is mixed for at least fifteen minutes.

EXAMPLE 1

Following the above procedure, the composition set forth below was formulated.

| Ingredients | % By Weight |
|---|---|
| Deionized Water | 31.0 |
| Ammonium Alpha-Olefin Sulfonate (AOS) (15% active*) | 51.0 |
| Ammonium Phosphate - monobasic | 0.2 |
| Citric Acid | 0.5 |
| Distearyl Dimethyl Ammonium Chloride | 0.5 |
| $C_{20-40}$ Alcohol (Petrolite's Unilin 425) | 3.0 |
| Cocodiethanolamide (Standamid KD) | 4.0 |
| LUVIQUAT FC 905 (40% active) | 3.0 |
| Silicone (Union Carbide L-45) 60,000 cps | 4.0 |
| Perfume | 0.8 |
| Preservative | 0.5 |
| Color | 0.71 |
| Final pH = 5.3 | |

*Ammonium AOS, Witconate, 29.45% active

Surprisingly, studies showed that the above formulation (as well as that of Example 2 containing MERQUAT 100) was stable only in the presence of AOS. Replacing AOS with other surfactant systems such as sodium or ammonium lauryl sulfate produced undesirable results with respect to product stability.

The conditioning efficacy of the above formulation containing LUVIQUAT FC 905 was evaluated by wet combing and compared against conventional brand hair conditioning shampoos: (i) Rave All-In-One for damaged/permed hair, (ii) Optima 2-in-1 conditioning shampoo and (iii) a similar shampoo composition without LUVIQUAT FC 905. The results in Table 1 illustrate the superior conditioning efficacy of the formulation of Example 1 compared thereto.

The conditioning efficacy of the above formulation was evaluated and the results tabulated in Table 1.

TABLE 1

Conditioning Efficacy of Shampoo of Example 1

| | Average Wet Combing Scores* | |
|---|---|---|
| Test | Shampoo With LUVIQUAT FC 905 | Test Product |
| Shampoo formulation of Example 1 | | |
| vs. Rave All-In-One Conditioning Shampoo | 8.22 | 6.38 |
| vs. Optima 2-in-1 | 9.17 | 6.44 |
| vs. Shampoo with Silicone only, no LUVIQUAT FC 905 | 8.56 | 6.11 |

*Average of three tresses, each evaluated by a panel of six judges on a scale of 1 (worst) to 10 (best).

Statistical analysis of the above data shows that the difference in the test scores of ammonium AOS based shampoo containing LUVIQUAT FC 905 as compared to each one of the three test products is significant beyond the 95% confidence level (p=0.0001), demonstrating superiority of the FC 905 based shampoo for conditioning efficacy.

Additional studies also showed that the formulation of Example 1 also provided superior post-shampoo cuticle protection as determined by quantitatively measuring cuticle loss during wet combing.

To test post-shampoo cuticle protection, multiple hair tresses were shampooed using the test products and rinsed extensively with tap water. Each hair tress was then combed at 100 strokes. After five strokes each, the comb was rinsed in a beaker containing 100 ml of distilled water and, after ten strokes, each tress was also rinsed in the same water. The water solution from each tress was then analyzed for dissolved/suspended protein material by the Lowry method [Lowry et al, *J. Biol. Chem.*, Vol. 193, pages 265–275 (1951)]. The results of this test are shown in Table 2 below.

TABLE 2

Comparison of LUVIQUAT FC 905 Shampoo vs. Rave for Post-Shampoo Cuticle Damage During Combing

| Treatment | Cuticular Protein Removed (mg/gm Hair) |
|---|---|
| Ammonium AOS, FC 905 + Silicone | |
| Tress #1 | 0.235 |
| Tress #2 | 0.142 |
| Tress #3 | 0.151 |
| Average | 0.176 |

TABLE 2-continued

Comparison of LUVIQUAT FC 905 Shampoo vs. Rave for Post-Shampoo Cuticle Damage During Combing

| Treatment | Cuticular Protein Removed (mg/gm Hair) |
|---|---|
| Rave All-In-One* | |
| Tress #1 | 0.431 |
| Tress #2 | 0.315 |
| Tress #3 | 0.417 |
| Average | 0.388 |
| Ratio: Rave vs. Ammonium AOS | 2.2 |

*Commercial conditioning shampoo

The above results clearly show that the amount of cuticular material removed during combing from hair shampooed with the formulation containing ammonium AOS, LUVIQUAT FC 905 and silicone is minimal as compared to the hair shampooed with Rave, demonstrating that the former provides cuticle protection during combing.

Further studies also showed that hair treated with Rave has a very severe flyaway problem, whereas no such problem is seen with hair treated with FC 905 conditioning shampoo washed up to five times.

EXAMPLE 2

Following the procedure of Example 1, the following composition was formulated.

| Ingredients | % By Weight |
|---|---|
| Deionized Water | 31.5 |
| Ammonium AOS* | 51.0 |
| Ammonium Phosphate - monobasic | 0.2 |
| Distearyl Dimethyl Ammonium Chloride | 0.5 |
| $C_{20-40}$ Alcohol (Petrolite's Unilin 425) | 3.0 |
| Cocodiethanolamide (Standamid KD) | 4.0 |
| MERQUAT 100 (~40% active) | 3.0 |
| Silicone (Union Carbide L-45) 60,000 cps | 4.0 |
| Perfume | 0.8 |
| Preservative | 0.5 |
| Color | 0.71 |
| Final pH = 6.5 | |

*Ammonium AOS, Witconate Lot #5130-190, 29.45% active

The above formulation was found to be stable only in the presence of AOS; replacing AOS with other surfactant systems such as sodium or ammonium lauryl sulfate produced undesirable results with respect to product stability. Furthermore, this formulation was also very effective to condition hair during shampooing.

TABLE 3

Conditioning Efficacy of a Shampoo of Example 2

| Test | Average Wet Combing Scores* |
|---|---|
| Shampoo formulation of Example 2 containing MERQUAT 100 | 8.9 |
| vs. Rave All-In-One Conditioning Shampoo | 7.5 |

*Average of three tresses, each evaluated by a panel of six judges on a scale of 1 (worst) to 10 (best). Observed differences all at p = 0.0001 level.

The following examples demonstrate superiority of alpha-olefin sulfonates as anionic surfactants in shampoo formulations as compared with conventionally employed surfactants.

Various investigators have shown hair damage due to shampooing [Kelly et al, *J. Soc. Cosmet. Chem.*, Vol. 33, page 203 (1982); Gould et al, *J. Soc. Cosmet. Chem.* Vol. 36, page 53 (1985)]. It has also been demonstrated that a large amount of cuticle, the outer protective layer of hair, erodes during the actual shampooing process [Okumura, 4th Int. Hair Sci. Symp., Syburg, West Germany (November 1984)]. It is well established that the cuticle not only provides a physical barrier to the inner components, but also influences the cosmetic properties of hair such as luster, feel, combability, etc.

EXAMPLE 3

Most shampoos contain an anionic surfactant, usually the sodium or ammonium salt of lauryl sulfate or laureth sulfate, as a major ingredient, although other surfactant, thickening and conditioning agents, colors and fragrances are also commonly present. Since hair is a proteinaceous material, measuring the amount of hair protein dissolved by various surfactants can serve as an indicator of hair damage. Using this approach, a number of surfactants were screened for mildness. The procedure involved shaking hair samples in a surfactant solution for a certain time period followed by analysis of the solution for protein concentration.

To study the effect of surfactants on protein solubilization from hair, 200 mg of ~½-inch long hair from tip ends were transferred to each of a series of 50 ml Erlenmeyer flasks containing 20 ml of a given surfactant solution (5% AI). The flasks were shaken on the Burrel Wrist-action shaker for 24 hours. At the end of the shaking period, each sample was analyzed to determined protein concentration in the surfactant solution by the Lowry method, one of the most widely used techniques for the measurement of protein in biological samples, which was slightly modified for purposes of this invention. To complete the analysis, 0.5 ml of the turbid solution was added to a 16×125 mm test tube containing 0.5 ml of 1N NaOH. The contents of the tube were mixed well and allowed to sit at room temperature for thirty minutes to solubilize the large protein fragments in the solution. At the end of the incubation period, 1 ml of Cu-carbonate solution was added. Cu-carbonate solution was prepared fresh each day by mixing 1 ml each of $CuSO_4$ solution (1% w/v) and potassium tartrate solution (2% w/v) with 20 ml of $Na_2CO_3$ solution (10% w/v). The tubes containing Cu-carbonate treated alkaline protein solution were incubated at room temperature for fifteen minutes. At the end of the incubation period, 3 ml of Folin-phenol solution, prepared by diluting 5.0 ml of 2N Folin-phenol reagent with 50 ml of distilled water was added forcibly and mixed immediately. The samples were further incubated for forty minutes and the absorbance of each sample was determined in a spectrophotometer (Bausch & Lomb's Spectronic 20) at a wavelength of 750 nm. The protein concentration of each sample was determined from a standard curve prepared separately for each surfactant system containing crystalline bovine serum albumin as standard and was assayed under conditions identical to the test samples. The following equation, derived from the simple regression analysis of the standard curve data, was used to calculate the protein concentration of the test samples:

$$\text{Concentration} = \text{Slope} \times \text{Absorbance} - \text{Intercept on Y axis}$$

Based on these procedures, it was discovered that alpha-olefin sulfonate is very mild to hair as compared to sodium lauryl sulfate (Table 3, t=2.94, data significant at 95% CL).

TABLE 3

Effect of Various SUrfactants on the Solubilization of Hair Protein

| Surfactant (5%) | Protein Solubilized (mg/gm Hair*) |
| --- | --- |
| Sodium Lauryl Sulfate (SLS) | 10.26 |
| Ammonium Lauryl Sulfate (ALS) | 9.36 |
| Water (Control) | 8.42 |
| Alpha-Olefin Sulfonate-Na (AOS) | 7.80 |

*Each value represents a cumulative average of 6–15 samples of multiple experiments.

The above surfactants were tested without any pH adjustment; the pH of the SLS, ALS and AOS solutions as tested was ~9.5, 7.5 and 7.3, respectively. Further studies showed that lowering the pH of the AOS solution from 7.3 to 3.5 reduced the amount of protein solubilized from 7.8 to 3.9 mg/gm hair, demonstrating that the surfactant induced hair damage can be further minimized by lowering the pH of the surfactant solution. It should be noted that AOS is very stable under acid conditions, whereas other surfactants such as SLS, SLES, ALS and ALES are very susceptible to hydrolysis at low pH and, therefore, not suitable for product applications at low pH.

The following example demonstrates the superiority of ammonium alpha-olefin sulfonate as an anionic surfactant compared to other alpha-olefin sulfonate salts.

EXAMPLE 4

The procedure of Example 3 was followed to test the protein solubilization characteristics of various alpha-olefin sulfonates. As shown in Table 4, the amount of protein dissolved by $NH_4$ AOS is significantly lower as compared to Na AOS (p=0.0263). Additional studies using a foam booster, namely, cocodiethanolamide (Standamid KD), commonly used in shampoos in combination with the same surfactants further supports the above conclusions (Table 4). These experiments were conducted at pH 3. Furthermore, studies also showed that $NH_4$ AOS (Standamid KD) composition can be easily thickened using $NH_4Cl$, whereas Na AOS (Standamid KD) composition was very difficult to thicken even at high salt concentrations. As shown in Table 4, the viscosity of $NH_4$ AOS (Standamid KD) formulation was found to be 4,000 cps at 2.5% $NH_4Cl$ concentration, whereas Na AOS composition even at 4% salt had a viscosity of only 800 cps, which is well below the desired levels (>3,000 cps) for shampoo formulations.

TABLE 4

| Surfactant System | Protein Solubilized (mg/gm Hair*) | Viscosity (cps**) |
| --- | --- | --- |
| AOS - sodium salt | 5.49 | |
| AOS - ammonium salt | 4.35 | |
| AOS - sodium salt + Standamid KD | 5.58 | <120 @ 2.5% NaCl<br>800 @ 4% NaCl |
| AOS - ammonium salt + Standamid KD | 3.28 | 4,000 @ 2.5% $NH_4Cl$ |

*Average of multiple samples at pH 3
**Brookfield Viscometer, Model RV, Spindle #5

The above AOS compositions were thickened at pH 3. Similar observations were made when the viscosity of Na or $NH_4$ AOS (Standamid KD) compositions were studied at pH 7, demonstrating that, regardless of the pH, the $NH_4$ salt of AOS is relatively very easy to thicken, whereas AOS as the sodium salt is unsuitable for thickening with salts. Clearly, this offers additional advantages for using $NH_4$ AOS rather than Na AOS in shampoo formulations.

EXAMPLE 5

Using the protein solubilization test method, a number of prototype shampoo formulations as shown in the following example were prepared and tested for mildness and other desired shampoo characteristics. Test results were found to be satisfactory.

An example of the shampoo formulation follows:

| Ingredients | % w/w |
| --- | --- |
| $NH_4$ AOS | 57.45 (26.1% AI) |
| Cocodiethanolamide (Standamid KD) | 3.00 |
| Citric Acid to pH 3 | 2.00 |
| $NH_4Cl$ | 2.50 |
| Distilled Water | Q.S. |
| TOTAL | 100.00 |

EXAMPLE 6

The following composition was formulated as a low pH shampoo.

| Ingredients | Wt. % |
| --- | --- |
| Ammonium AOS (Witco) | 15.00 (AI) |
| $C_{20-40}$ Alcohol (Unilin 425) | 3.00 |
| Standamid KD | 4.00 |
| Dow Silicone X2-8565 | 3.00 |
| Ammonium Phosphate, monobasic | 0.20 |
| Citric Acid | 2.00 |
| Distilled Water, filtered and irradiated | Q.S. |
| TOTAL | 100.00 |
| Viscosity (Brookfield) | ~3,000 cps |
| Final pH | 3.0 |

To test the above formulation for mildness, a hair tress (~12 inches long and weighing about 3 grams) was shampooed with the test product. The tress was then rinsed extensively with lukewarm tap water, combed and dried with a hair dryer. The hair from this tress was then cut from the tip end into ~½-inch pieces to obtain 800 mg of the clippings. 200 mg of the clippings were added to each of the four Erlenmeyer flasks (50 ml capacity) containing 20 ml distilled water. The flasks were shaken for 24 hours and the solution was analyzed for protein solubilized as described in Example 2 above. For comparison, one of the leading commercial shampoos, Pert Plus, was also tested in the same manner as described above. This test simulates the effects of a shampoo during rinsing. These studies showed the results set forth in Table 5.

TABLE 5

| Product | Protein Solubilized* mg/gm Hair |
| --- | --- |
| Pert Plus | 1.81 |
| $NH_4$ AOS Shampoo | 1.35 |

*Average of four samples

As shown above, the amount of protein solubilized by NH$_4$ AOS is significantly less as compared to Pert Plus (p=0.017), evidencing that NH$_4$ AOS based shampoo is less damaging to hair. Furthermore, the above two formulations were also tested and compared for conditioning properties as evaluated by wet combing and other characteristics such as flyaway and sensory feel. The results showed no perceptible differences between the two products.

EXAMPLE 7

An Additional prototype shampoo formulation as shown in the following example was prepared and tested for mildness and other desired shampoo characteristics, including style control and conditioning. Test results were found to be satisfactory.

| | |
|---|---|
| D. Water | Q.S. |
| Merquat 100 | 1.60 |
| Tego Beteine | 3.20 |
| SCS | 1.60 |
| D. Water | 3.00 |
| Polymer-JR. 30M | 0.40 |
| NaH$_2$PO$_4$ | 0.16 |
| Unilin 425 | 2.50 |
| (Distearyl Dimmonium (Chloride) (TA-100) | 0.20 |
| Perfume | 1.00 |
| Preservative | 0.75 |
| Color | Q.S. |
| NH$_4$ AOS | 14.50 |
| Light Mineral Oil | 0.40 |

We claim:

1. A low pH aqueous hair conditioning shampoo stable under acid condition in emulsion or suspension form consisting essentially of:

(i) 10 to 25% by weight of an anionic surfactant consisting of an alpha-olefin sulfonate;

(ii) 0.3 to 6% by weight of a cationic polymer having a hair conditioning effect and a charge density greater than about 200 selected from the group consisting of a copolymer comprising vinylimidazole and vinylpyrrolidone wherein the molar ratio of said vinylimidazole to said vinylpyrrolidone is at least about 5:1, a homopolymer of dimethyldiallylammonium halide, polyethyleneimine and mixtures thereof;

(iii) from 0 to 8% by weight of a second dispersed water insoluble hair conditioning agent different from component (ii);

(iv) from 0.3 to 8% by weight of at least one dispersing agent sufficient to stabilize said aqueous shampoo in emulsion or suspension form, said dispersing agent comprising a long chain saturated primary aliphatic alcohol or a derivative thereof having an average of 24 to 45 carbon atoms in said chain; and (v) the remainder water.

2. A hair conditioning shampoo according to claim 1 wherein said anionic surfactant is a water-soluble salt of an alpha-olefin sulfonate.

3. A hair conditioning shampoo according to claim 2 wherein said salt is ammonium alpha-olefin sulfonate.

4. A hair conditioning shampoo according to claim 1 containing 0.5 to 2% of said cationic copolymer.

5. A hair conditioning shampoo according to claim 1 containing 0.5 to 4% of said dispersed water-insoluble hair conditioning agent.

6. A hair conditioning shampoo according to claim 1 containing 1 to 5% of said dispersing agent.

7. A hair conditioning shampoo according to claim 1 wherein said dispersing agent functions to render said emulsion or dispersion pearlescent.

8. A hair conditioning shampoo according to claim 1 additionally containing shampoo adjuvants.

9. A hair conditioning shampoo according to claim 1 wherein said second water-insoluble hair conditioning agent is selected from the group consisting of silicones, aminosilicones, polyalkylenes and oxidized derivatives thereof, paraffins, petrolatums, microcrystalline waxes, $C_{18-36\ (mixed)}$ fatty acids and triglycerides thereof and mixtures thereof.

10. A low pH aqueous hair conditioning shampoo stable under acid condition in emulsion or suspension form consisting essentially of:

(i) 10 to 25% by weight of an anionic surfactant consisting of an alkali metal or ammonium alpha-olefin sulfonate surfactant derived from $C_{14}$ to $C_{18}$ alpha olefins;

(ii) 0.3 to 6% by weight of a cationic polymer having a hair-conditioning effect and a charge density greater than about 200 selected from the group consisting of a copolymer comprising vinyl imidazole and vinylpyrrolidone wherein the molar ratio of said vinylimidazole to said vinylpyrrolidone is at least about 5:1, a homopolymer of dimethyldiallylammonium halide, polyethyleneimine and mixtures thereof;

(iii) 0.5 to 4% by weight of a silicone hair conditioning agent;

(iv) 0.3 to 8% by weight of at least one dispersing agent sufficient to stabilize said aqueous shampoo in emulsion or suspension form, said dispersing agent comprising a long chain saturated primary aliphatic alcohol or a derivative thereof having an average of 24 to 45 carbon atoms in said chain; and (v) the remainder water.

11. The hair conditioning shampoo according to claim 10 wherein said surfactant is an ammonium alpha-olefin sulfonate.

12. The hair conditioning shampoo according to claim 11 wherein said silicone hair conditioning agent is an aminosilicone.

13. The hair conditioning shampoo according to claim 1 wherein said cationic polymer comprises a copolymer of 95% vinylimidazole and 5% vinyl pyrrolidone.

\* \* \* \* \*